United States Patent [19]
Schawartz et al.

[11] Patent Number: 4,581,348
[45] Date of Patent: Apr. 8, 1986

[54] SYNERGISTIC PHARMACEUTICAL COMPOSITIONS

[75] Inventors: József Schawartz; Maria Hornyák; Tamás Szuts; József Lengyel; Károly Lapis; János Fehér; Sándor Virág; Gyula Sebestyén; Katalin Kállóy, all of Budapest; Katalin Mármarosi, Biatorbágy, all of Hungary

[73] Assignee: Chinoin Gyogyszer es Vegyeszeti Termekek Gyara R.T., Budapest, Hungary

[21] Appl. No.: 629,678

[22] Filed: Jul. 11, 1984

[30] Foreign Application Priority Data

Jul. 11, 1983 [HU] Hungary ............................. 2463/83

[51] Int. Cl.[4] .................. A61K 31/385; A61K 31/675
[52] U.S. Cl. ........................................ 514/76; 514/80; 514/893; 514/894
[58] Field of Search .................. 424/200, 255; 514/80, 514/76, 893, 894

[56] References Cited

U.S. PATENT DOCUMENTS 4,182,770 1/1980 Behpour et al. ................ 424/273 R
4,499,076 2/1985 Ohashi et al. ....................... 424/145

OTHER PUBLICATIONS

Trends in Pharmacological Science, 82, vol. 3, No. 9, pp. 365–367 (Sep. 1982).
Chem. Abstracts 90:98085n (1979).
Chem. Abstracts 93:161288k (1980).
Chem. Abstracts 94:23257u (1981).
Chem. Abstracts 96:14950d–14951e (1982).

*Primary Examiner*—Douglas W. Robinson
*Attorney, Agent, or Firm*—Karl F. Ross; Herbert Dubno

[57] ABSTRACT

The present invention relates to synergistic pharmaceutical compositions for the treatment of liver disorders comprising 5-aminoimidazole-4-carboxamide orthophosphate (AICA-phosphate) as active ingredient in association with vitamins, preferably with vitamin B and/or E and optionally with other pharmaceutical excipients.

7 Claims, No Drawings

SYNERGISTIC PHARMACEUTICAL COMPOSITIONS

FIELD OF THE INVENTION

The present invention relates to a synergistic pharmaceutical composition for the treatment of liver disorders and a method for the treatment of liver disorders by the aid of the synergistic compositions.

BACKGROUND OF THE INVENTION

The development of liver diagnostic procedures (biopsy, endoscopy, sonography etc.) has enabled the earlier and more exact recognition of liver disorders. The early diagnosis should be followed by timely intervention taking into consideration the progredial feature of the disease, as there are substantially fewer therapeutical methods for the treatment of the disease than diagnostic procedures to discover it. Simultaneously the prevalence of liver disorders has increased rapidly in the last decades.

According to epidemiologic tests it has become obvious that the number of liver disorders shows an increasing tendency (Statistic Year-Book of 1949 to 1955; issued by the Central Statistical Office, Budapest, 1957; Statistic Year-Book of 1970, issued by the Central Statistical Office, Budapest, 1971). It shows, that three times as many people died from liver cirrhosis in 1977 than in 1955.

A large number of those dying as a result of liver cirrhosis die at the age of between 40 and 59, i.e. during working age. Thus in 1970 35%, whereas in 1978 41% of the patients died at the age of 40 to 50 due to liver cirrhosis.

These data are in accordance with the conclusions drawn from mortality statistics relating to 26 countries on 4 continents, indicating that the prevalence of liver cirrhosis increased worldwide to such an extent, that one can speak of an epidemic of liver cirrhosis.

Among the causative factors primarily alcoholism appears to be responsible for this intensive spread of liver diseases. The most frequent types of liver disorders are fatty liver, alcoholic hepatitis and alcoholic cirrhosis.

The ultimate therapeutic treatment of liver disorders cannot be considered to have been discovered [Orvosi Hetilap 112:386 (1971); Z. ärztl. Fortbildung, 68, 234 (1974); Knoll: Gyogyszertan (1974); Szekeres: Orvosi gyogyszertan (1980)].

The cause inducing the liver damaging process is irrelevant; it can be said as a fundamental principle, that the result of the pathological process is determined by the equilibrium between the deleterious effect of the noxious agent (virus, alcohol) and the positive effect of the regenerating activity of liver tissue. Nowadays there is no possibility to eliminate the noxious agents, especially in the case of developed and progrediated liver diseases. The only realistic aim to be achieved by the therapeutic treatment is to enhance the natural regenerating property of liver tissue. Knowing the complexity of liver function, this treatment cannot be in the form of a monotherapy.

The success of polytherapeutic treatments depends on finding pharmaceutical compounds for the preparation of the pharmaceutical combinations capable of influencing the basic pathological process. Possessing such compounds one can work out such combinations which may be suitable for the planning of pharmaceutical compositions of several "points of attack".

The precursors of amino acids can be considered such pharmaceutical compounds for treatment of liver disorders [Dtsch., Med., Wschr., 78 1331 (1953); Dtsch., Med., Wsch., 81 573 (1956)]. However, the nucleotides or nucleosides in question are generally unable to penetrate through the cell-membrane and they are often toxic as well [Angew. Che., 82, 730 (1970); J. Med. Chem. 15, 1334 (1972)]. The problem is increased by the fact, that the preparation of these compounds is very expensive and complicated.

Therefore the search has been directed to such chemical structures which can easily penetrate into the cell and can there be transformed into nucleotides.

It is wellknown in the art, that the fatty liver induced by alcohol, characterized by triglyceride accumulation and ATP decrease, cannot be normalized by administration of guanine, GTP or ATP [Arch., Int. Pharmacodyn. 232, 302 (1978)]. Though the fatty liver thus induced and the ATP decrease can be normalized by intraperitoneal adenine (6-aminopurine) administration, a part of the 6-aminopurine is transformed into 8-oxyadenine and 2,6-dioxyadenine metabolites, which severely damage the kidney-function [J. Pharmacol. exper. Ther. 140, 20 (1952)].

The administration of the nucleotide precursor orothic acid also leads to the disorder to the lipid metabolism of liver and results in fatty liver [J. Biol. Chem. 238, 2464 (1963)]. This fatty liver as well as the fatty liver caused by ethionine can be normalized by the administration of adenine (6-aminopurine), but it cannot be used for therapeutic purposes due to its nephrotoxic effect referred above.

The purine precursor 5-aminoimidazole-4-carboxamide (AICA) [Science, 112, 634 (1950); J. Biol. Chem. 196, 513 (1952)] was used for therapeutic treatment [J. Med. Sci. 15, 171 (1964)] in the form of its salt formed with orothic acid under the trade name of Aicorat ® [Ann. Histochim. 14, 79 (1969)].

Tha Aicorat ® was not therapeutically effective because the orothic acid itself is a liver damaging agent [J. Biol. Chem. 238, 2464 (1963)], thus in the orothic acidic salt of AICA the advantageous effect of AICA was nullified by the harmful effect of the other component.

We thus targeted our efforts at finding such imidazole carboxamide derivatives which possess the advantageous effects of purine precursor but are free of the negative effects reported in the case of Aicorat ®.

Exp. Path 15, 271–287 (1978) reports on the advantageous pharmacological properties of 5-aminoimidazole-4-carboxamide orthophosphate (further: AICA-phosphate) in the treatment of liver artificially damaged by carbon tetrachloride.

It is known, that AICA-phosphate can be prepared by reacting 2-amino-2-cyano acetamide with formamidine ortho phosphate (Hungarian patent specification No. 164,397). The raw AICA-phosphate thus obtained is not suitable for therapeutical purposes.

SUMMARY OF THE INVENTION

We have now found that pure AICA-phosphate suitable for therapeutical use can be prepared in high purity by reacting AICA base with orthophosphorous acid in aqueous alcoholic medium, e.g. a 50% by weight ethanolic solution of 4,5-aminoimidazole-5,4-carboxamide with orthophosphoric acid and recovering the crystalline AICA-phosphate from the solution.

We found, that the AICA-phosphate prepared as given above and the compositions containing AICA-phosphate and vitamins preferably vitamin B and E can preferably be used in the treatment of alcoholic fatty liver and other liver disorders of different origin leading to cirrhosis or hepatitis as they inhibit the pathological progression of the diseases.

DETAILED DESCRIPTION OF THE INVENTION

On examination by thin-layer chromatography the high purity AICA-phosphate is uniform, its purity is practically 100%, its melting point is 192°–194° C. (The AICA-phosphate prepared previously had a melting point of 190° C. and decomposed at this temperature).

The highly pure AICA-phosphate used for the treatment in itself shows the following properties:

1. In acute toxicity tests the compound administered intraperitoneally or intravenously does not induce toxic symptoms even in higher doses [$LD_{50} > 5000$ mg/kg when rodents are administered the drug orally, while $LD_{50} > 1000$ mg/kg when the drug is administered intravenously], therefore AICA-phosphate can be regarded as an atoxic compound.

The chronic (6 months) toxicity tests on rodents and other animals showed, that even a 15–20 fold amount of the planned therapeutic dose does not result in toxic symptoms.

2. When examining the generally pharmacodynamic effects of AICA-phosphate it can be stated, that it has no significant effect on the other organs, organ systems in the classical pharmacological tests, its effect on the liver can be considered as being organ specific.

3. When examining the liver specific effect of the compound, it can be concluded, that AICA-phosphate exhibits several advantageous properties. According to experiments carried out by using radioactive AICA-phosphate, the increase of liver serum quotient could be observed with the advance of the time of treatment. The radioactive AICA-phosphate can be detected in the RNS fraction of liver cells. Upon the treatment with AICA-phosphate the protein synthesis is enhanced and the amount of glycogen is increased in the liver cells. The fatty retrogradation of liver caused by ethionine is substantially reduced by AICA-phosphate. (The liver damage caused by ethionine is very similar to human fatty liver caused by alcohol). [Trends in Pharmacological Sciences 82, vol. 3, No. 9, pages 365–367].

4. In immune reactions the number of both the active and the total E rosetta increases upon the treatment with AICA-phosphate.

The chronic liver disorders are generally characterised by the lack of phosphate anions, more exactly the pathological decrease of the intracellular concentration of phosphate ions. This lack of phosphate ions is often a result of acute or more often chronic alcoholism [Clin. Chim. Acta 78, 353 (1978)].

The effect of the other AICA-salts, e.g. AICA-hydrochloride, AICA-pyrophosphate and AICA-orothate on artificially damaged liver is not as good as that of the AICA-phosphate. One of the explanations is that the phosphate ions administered together with AICA-phosphate take part in the synthesis of α-D-ribofuranose-1-pyrophosphate-5-phosphate which plays an important role in the building up of nucleotides from precursors.

Regarding the basic effect of AICA-phosphate, we were aiming at working out a composition which is suitable not only for the increasing of liver-protecting (regenerative) properties of liver, but for the symptomatic as well as pathogenic treatment of alcoholic fatty liver.

We have found, that the effect of AICA-phosphate can be significantly increased if it is administered in a combination with vitamins, preferably with B or E vitamins.

The activity of the components and the combination was examined on liver damaged by ethionine. The activity of the combinations expressed by giving the triglyceride content of the liver. The triglyceride content of liver after the administration of 250 mg/kg of ethionine on the second day was taken as a basis, the results listed in the table are average values obtained on 10 animals. CFY male rats weighing 200 g were used in the experiments. The results are listed in Table I.

TABLE I

| Treatment (p.o) | Triglyceride content of liver mmole/kg | Decrease (D) % |
|---|---|---|
| ethionine 250 mg/kg | 0.042 | — |
| ethionine 250 mg/kg + AICA-phosphate 200 mg/kg | 0.031 | 26 |
| ethionine 250 mg/kg + AICA-phosphate 200 mg/kg + vit. $B_1$ 0.1 mg/kg | 0.022 | 47.7 |
| ethionine 250 mg/kg + AICA-phosphate 200 mg/kg + vit. E 10 mg/kg | 0.023 | 47.5 |

The data of Table I clearly show that the vitamins used significantly increased the activity of AICA-phosphate.

The histological tests show that a diffuse, great decrease in the degeneration of the liver is developed as a result of the treatment with 250 mg/kg of ehtionine by the second day after the treatment, while on the 5th day the histological pathography is dominated by the beneficial decreased fatty degeneration. 200 mg/kg of AICA-phosphate administered p.o. inhibits the liver from becoming fatty and this activity is intensified by vitamins $B_1$ or E.

The results of the histology tests are listed in Table II.

TABLE II

| Toxic agent | Treatment | The semi-quantitative evaluation of liver fattening according to oil-red.-o tinction /x |
|---|---|---|
| ethionine | — | on the 2nd day +++ <br> on the 5th day ++(+) |
| ethionine | AICA-phosphate | on the 2nd day ++(+) <br> on the 5th day +(+) |
| ethionine | AICA-phosphate + vitamin $B_1$ | on the 2nd day ++ <br> on the 5th day + |
| ethionine | AICA-phosphate + vitamin E | on the 2nd day ++ <br> on the 5th day + |

The doses administered:
ethionine: 250 mg/kg p.o.
AICA-phosphate 200 mg/kg p.o.
Vitamin $B_1$ 0.1 mg/kg p.o.
Vitamin E 10 mg/kg p.o.
(x the average values obtained according to 5 tests).

The invention relates to synergistic pharmaceutical compositions suitable for the treatment of liver disorders comprising as active ingredient 5-aminoimidazole-4-carboxamide orthophosphate and vitamins, preferably vitamin B₁ or E optionally in association with other pharmaceutical excipients.

The composition according to the invention preferably contains 20 to 60% by weight of 5-aminoimidazole-4-carboxamide orthophosphate and 0.01 to 20% by weight of vitamins.

The composition according to the invention can be formulated into a form which can be administered orally, e.g. tablets, dragées, capsules. The tablets preferably contain 100 or 200 mg of the active ingredient.

The details of the invention are illustrated by the following, non-limiting examples.

PREPARATION OF HIGH PURITY AICA-PHOSPHATE 34.48 g of 4(5)-amino-imidazole-5(4)-carboxamide-monohydrate (AICA) are dissolved in 200 ml of 50% by volume aqueous ethanol under stirring at 45°–50° C., and the solution is clarified by charcoal. Thereafter 27.7 g of 85% orthophosphoric acid are charged, about 5 minutes after the addition the first crystals occur. Then the reaction mixture is stirred for 20 minutes and cooled with ice water for 2 hours. The solution is filtered, washed with 30 ml of anhydrous ethanol and dried. 51.2 g (95%) of colorless crystals are obtained. M.P: 192°–194° C.

On examination by thin-layer chromatography the high purity AICA-phosphate is uniform, its purity is practically 100%, its melting point is 192°–194° C. (The AICA-phosphate prepared previously had a melting point of 190° C. and decomposed at this temperature).

EXAMPLE 1

| AICA-phosphate | 200 mg. |
| --- | --- |
| Thiaminehydrochloride (vit. B₁) | 5 mg. |
| Riboflavin (vit. B₂) | 5 mg. |
| Pyridoxiniumchloride (vit. B₆) | 6 mg. |
| di-α-Tocolferolacetate (vit. E) | 4 mg. |
| Talcum | 20 mg. |
| Lactose | 50 mg. |
| Amylum | 50 mg. |
| Stearine | 8 mg. |
| Luviscol (VA. 64) | 8 mg. |
| Microcrystalline cellulose (Avicel) | 44 mg. |
| | 400 mg. |
| Coating of the dragee: | |
| Carbowax 6000 | 1.0 mg. |
| Titanium dioxide | 4.0 mg. |
| Methyl cellulose | 6.8 mg. |
| Luviscol (VA. 64) | 6.8 mg. |
| Talcum | 21.4 mg. |
| | 40 mg. |

The AICA-phosphate, starch and lactose are homogenized. Luviscol and stearine are dissolved in isopropanol and the powder mixture is granulated by the solution thus obtained. The granules are dried at 40° to 50° C. Thereafter regranulated on a sieve of 16 mesh.

Then the homogenized vitamins, lactose and the microcrystalline cellulose are mixed to the granules, then the mixture is dried until the moisture content of the granules is 1.5%. Biconvex dragée grains are pressed from the granules by a conventional manner.

The coating is carried out in an overpressurized apparatus according to the rules of producing film dragée known per se.

EXAMPLE 2

| first step | AICA-phosphate | 200 mg. |
| --- | --- | --- |
| | Nicotinamide | 9 mg. |
| | Methionine | 50 mg. |
| | folic acid | 1 mg. |
| | Luviscol (VA. 64) | 4 mg. |
| | Stearine | 4 mg. |
| second step | Lactose | 108 mg. |
| | Amylum | 12 mg. |
| | Gelatine | 2 mg. |
| | | 400 mg. |

First Step

Luviscol and stearine are dissolved in isopropanol, thereafter the AICA-phosphate is granulated. The granulate is dried then regranulated on an industrial sieve of 16 mesh and the other components of the first step are mixed with the granulate.

Second Step

Gelatine is dissolved in distilled water on a water bath at 70° C. after swelling and the mixture of lactose and amylum is wetted by this solution. The wetted mixture is granulated on a sieve of 16 mesh thereafter dried at 60° C. by fluidization technique. The granulates obtained in the first and second step are homogenized and biconvex dragée grains are pressed. The coating is carried out according to Example 1.

EXAMPLE 3

| First step | AICA-phosphate | 200 mg. |
| --- | --- | --- |
| | Methionine | 50 mg. |
| | Ornihine asparginate | 25 mg. |
| | Luviscol (VA. 64) | 6 mg. |
| | Stearine | 4 mg. |
| Second step | Lactose | 100 mg. |
| | Amylum | 10 mg. |
| | Gelatine | 5 mg. |
| | | 400 mg. |

The dragée is prepared according to Example 2.

We claim:

1. A pharmaceutical composition for the treatment of alcoholic fatty liver, alcoholic hepatitis, or alcoholic cirrhosis which comprises as active ingredients 20 to 60% by weight of 5-amino-benzimidazole-4-carboxamide orthophosphate and 0.01 to 20% by weight of a vitamin selected from the group consisting of Vitamin B₁ and Vitamin E, along with a pharmaceutically acceptable excipient.

2. The pharmaceutical composition defined in claim 1 wherein the vitamin is Vitamin B₁.

3. The composition as claimed in claim 1 which comprises Vitamin B₁.

4. A method for the treatment of alcoholic fatty liver, alcoholic hepatitis, or alcoholic cirrhosis which comprises orally administering to a susceptible animal subject a therapeutically effective amount of the composition defined in claim 1.

5. A method for the treatment of alcoholic fatty liver, alcoholic hepatitis, or alcoholic cirrhosis which comprises orally administering to a susceptible animal subject a therapeutically effective amount of the composition defined in claim 2.

6. A pharmaceutical composition for the treatment of alcoholic fatty liver, alcoholic hepatitis, or alcoholic cirrhosis which comprises as active ingredient 200 parts by weight of 5-amino-benzimidazole-4-carboxamide orthophosphate and 0.1 part by weight of Vitamin $B_1$, along with a pharmaceutically acceptable excipient.

7. A method for the treatment of alcoholic fatty liver, alcoholic hepatitis, or alcoholic cirrhosis which comprises orally administering to a susceptible animal subject a therapeutically effective amount of the composition defined in claim 6.

* * * * *

UNITED STATES PATENT AND TRADEMARK OFFICE
CERTIFICATE OF CORRECTION

PATENT NO. : 4,581,348

DATED : April 8, 1986

INVENTOR(S) : Jozsef Schawartz et al

It is certified that error appears in the above-identified patent and that said Letters Patent is hereby corrected as shown below:

```
Claim 1, line 4 for "benzimidazole" read --imidazole--; and
Claim 6, line 4 for "benzimidazole" read --imidazole --.
```

Signed and Sealed this

Eighteenth Day of November, 1986

*Attest:*

DONALD J. QUIGG

*Attesting Officer*  *Commissioner of Patents and Trademarks*